United States Patent [19]

Weltlich et al.

[11] Patent Number: 4,476,489

[45] Date of Patent: Oct. 9, 1984

[54] MICROFINISH MEASUREMENT APPARATUS AND TECHNIQUE

[75] Inventors: Gary P. Weltlich, Massillon; Gary G. Wagner, Akron, both of Ohio

[73] Assignee: Inspection Technology, Inc., Akron, Ohio

[21] Appl. No.: 380,090

[22] Filed: May 20, 1982

[51] Int. Cl.³ .............................................. H04N 7/18
[52] U.S. Cl. ...................................... 358/107; 73/105
[58] Field of Search ...................... 358/106, 107, 93; 73/105

[56] References Cited

U.S. PATENT DOCUMENTS

| | | | |
|---|---|---|---|
| 3,133,149 | 5/1964 | Inaba | 358/20 |
| 3,320,799 | 5/1967 | Goody | 73/105 |
| 3,372,578 | 3/1968 | Harmon | 73/105 |
| 3,377,828 | 4/1968 | Harmon | 73/105 |
| 3,688,569 | 9/1972 | Murdoch | 73/105 |
| 3,733,598 | 5/1973 | Kato | 340/261 |
| 3,855,843 | 12/1974 | Yagiela | 73/105 |
| 4,106,333 | 8/1978 | Saljé | 73/105 |
| 4,126,036 | 11/1978 | Nilan | 73/105 |
| 4,148,027 | 4/1979 | Nowogrodzki | 73/105 |
| 4,149,187 | 4/1979 | Palmer | 358/107 |

*Primary Examiner*—Howard W. Britton
*Attorney, Agent, or Firm*—Oldham, Oldham, Hudak, Weber & Sand Co.

[57] ABSTRACT

An apparatus and technique for measuring microfinishes of workpieces at on-line speeds. A digitized image of a finished surface of a workpiece is generated. Under microprocessor control, a distribution of the digitized values is obtained. This distribution is compared against pre-stored distributions of known surface finishes to determine the type of finish of the workpiece and/or the acceptability of the finish. The comparison is obtained using curve matching techniques and by comparison of mean gray level values.

10 Claims, 6 Drawing Figures

4,476,489

MICROFINISH MEASUREMENT APPARATUS AND TECHNIQUE

TECHNICAL FIELD

The invention herein resides in the art of industrial inspection apparatus, and particularly of the noncontacting type. More specifically, the invention relates to a microfinish measurement apparatus and technique by which the finish of a surface is determined by the light reflectance characteristics thereof.

BACKGROUND ART

It is presently known that in many mechanical applications, the machined finish of a surface is of vital importance. For example, finishes must be maintained to close tolerances in bearings, races, cylinder walls, and the like. That close tolerance finishes are an everyday requirement in industry is evidenced by the fact that the Bureau of Standards has published classifications or standards for surface finishes. These classifications are graduated from designations of zero through fifty, the lower the designation, the smoother the finish. The standards are set with various parameters considered, such as the material of the finished surface of interest, the grit or coarseness of the finishing material, the method of finish or the like. It will be understood that there are various known finish methods, such as lapped, ground, blanchard, milled, profiled, and shape-turned.

Prior art methods of determining the finish of a surface have been of two basic types. The contacting type of sensor utilizes a stylus resolver such that the deflections of the stylus riding on the surface are converted to electrical signals indicative of surface smoothness. It will be readily appreciated that this type of measurement is akin to the stylus of a phonograph riding in a record groove. In use, the stylus-type resolvers measure deflections over a fixed area or lineal distance to determine surface finish.

There have also been previously known noncontact finish sensors, principally of the capacitive type. Here, a capacitive sensor rides over a surface in much the same manner as a proximity sensor, the capacitance of the sensor being matched to the surface material.

It will be readily appreciated that the finish sensors of the prior art are painstaking in use, being highly sensitive and adapted for laboratory use rather than use "on line." The prior art apparata and technique are used on a test sample basis, with workpieces being randomly selected from an assembly line for test in a laboratory to determine whether the line is meeting surface finish requirements. At best, the prior art achieves only a spot-check in an assembly line environment.

The prior art has taught stylus-type transducer finish sensors in U.S. Pat. Nos. 4,106,333; 3,133,149; 3,372,578; 3,320,799; 3,733,598; 4,126,036; and 3,377,828. Types of noncontacting finish sensors are taught in U.S. Pat. Nos. 3,688,569; 4,148,027; 4,149,187; and 3,855,843. Each of the prior art finish sensors taught by the aforementioned patents has the inherent drawback of requiring a laboratory environment to attain the desired test.

DISCLOSURE OF INVENTION

In light of the foregoing, there is presented a microfinish measurement apparatus and technique which may be used "on line" in an assembly line environment, testing the finish of each workpiece processed on the line.

According to another aspect of the invention, there is provided a microfinish measurement apparatus and technique which is reliable in use while being insensitive to changes in operating conditions as compared with prior art structures.

Still a further aspect of the invention is to provide a microfinish measurement apparatus and technique which is both highly accurate and automated.

Still a further aspect of the invention is to provide a microfinish measurement apparatus and technique which is of the nondestructive and noncontact type.

Still another aspect of the invention is to provide a microfinish measurement apparatus and technique which is basic in concept, relatively inexpensive to use, and readily adapted from state-of-the-art apparatus.

The foregoing and other aspects of the invention which will become apparent as the detailed description proceeds are achieved by apparatus for determining the finish of the surface of a workpiece, comprising: a source of illumination; means for passing the workpiece into proximity with said source of illumination; means for generating a digitized image of the workpiece and storing digitized pixels of said image; storage means for maintaining data corresponding to various preselected surface finishes; and means for comparing said digitized pixels with said data and detecting from such comparison the finish of the surface of the workpiece.

BRIEF DESCRIPTION OF DRAWINGS

For a complete understanding of the objects, techniques, and structure of the invention, reference should be had to the following detailed description and accompanying drawings wherein.

BEST MODE FOR CARRYING OUT THE INVENTION

Figure 1:
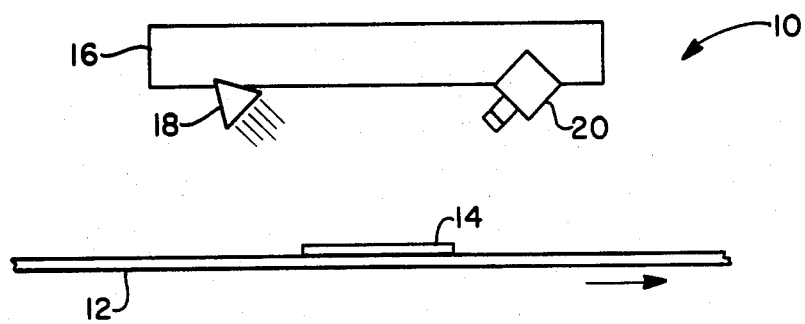
FIG. 1 is an illustrative view of the system of the invention.

Referring now to the drawings and more particularly FIG. 1, it can be seen that a microfinish sensor according to the invention is designated generally by the numeral 10. It will be noted that there is included a conveyor or other suitable transport means 12 for passing workpieces 14 along an assembly line or the like. The workpiece 14 would typically have a finished surface exposed toward a light source 18 and camera 20. The light source and camera are maintained in fixed registration with each other as by a fixed mounting plate 16. Accordingly, any movement of the light source 18 is accompanied by a like movement of the camera 20.

It will be appreciated from a review of FIG. 1, that the conveyor 12 passes the workpiece 14 within the field of view of the camera 20. The light source 18 casts light onto the finished surface of the workpiece 14, and the camera 20 receives and generates an image of such illuminated finished surface. This image is treated in a manner discussed below to determine the nature and/or acceptability of the finish of the workpiece 14.

Figure 2:
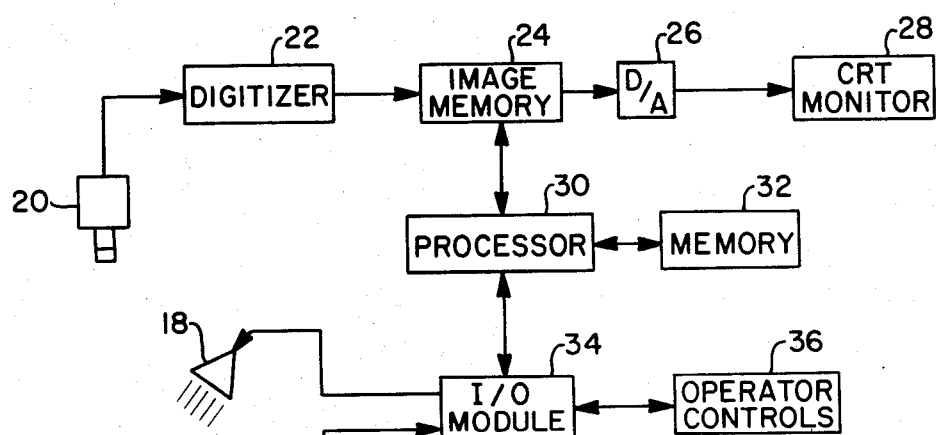
FIG. 2 is a schematic block diagram of the system of the invention.

As shown in FIG. 2, a digitizer 22 receives the analog output of the camera 20 and, in standard fashion, digitizes the image on a pixel-by-pixel basis. The array or matrix of pixels corresponding to the image viewed by the camera 20 is then passed to an image memory 24 wherein memory cells or registers receive the digitized values of the pixels comprising the image, maintaining such array of digitized data in a prearranged array, with each pixel having its own unique storage address. A digital to analog converter 26 may receive the digitized output of the image memory 24, convert the same to analog signals, and provide such image on an appropriate CRT or monitor 28.

Comprising the heart of the system of FIG. 2 is a microprocessor 30 which, in standard fashion, has associated therewith a memory array 32. The memory 32 maintains therein the programs for operation of the processor 30 while providing a scratch pad memory for operations and intermittent results, while further receiving and storing data therein corresponding to digitized pixel values of known finishes. Accordingly, the memory 32 would typically include some random access memory units and some read only memory units, the same being readily perceived by one skilled in the art.

The processor 30 communicates with an operator and peripheral equipment through an input/output module 34, as illustrated. It will be seen that through the module 34, the processor 30 may illuminate the lamp 18 at such time as the sensors 38 indicate that a workpiece 14 is within the proper field of view of the camera 20. When the processor 30 is advised by the switches 38 as to the presence of the workpiece 14, the processor 30 illuminates the light 18 until the workpiece passes. In similar fashion, the processor 30 causes the image memory 24 to receive a digitized image of the surface of the workpiece 14 via the camera 20 and digitizer 22. It will, of course, be appreciated that operator controls 36, such as a keyboard of the like, may be provided to allow an operator 36 to communicate with the processor 30 and the system as a whole.

For further details respecting the concept and structure illustrated in FIG. 2 reference should be had to copending patent application Ser. No. 207,748, filed Nov. 17, 1980, "Operator Programmable Inspection Apparatus." This application is assigned to Inspection Technology Inc., of Akron, Ohio, the assignee of the instant invention. Details respecting the programmability and operations of the basic system of FIG. 2 may be found in such copending application.

Figure 3:
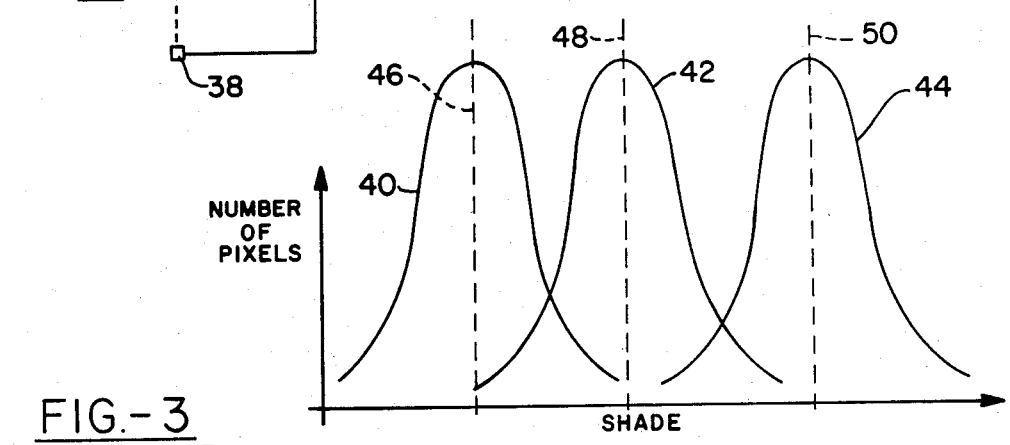
FIG. 3 is a set of normalized curves for reflectance from three different finishes.
Figure 4:
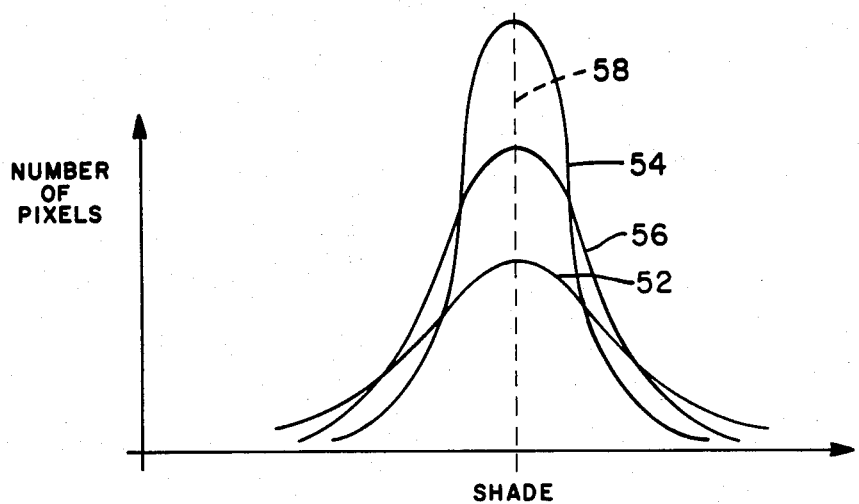
FIG. 4 is a set of normalized curves for reflectance of the same finish wherein the finish is obtained by three different finishing processes.

With reference now to FIGS. 3 and 4, certain key features of microfinishes are illustrated, as the same were discovered by applicants herein. FIG. 3 plots the number of pixels versus the shade or gray level of such pixels for three different surface finishes, all using the same finish technique, the curve for such finishes being respectively denominated 40, 42, 44. It will be appreciated that the digitizer 22 divides the image viewed by the camera 20 into a matrix or array of small, discrete, picture elements, or pixels, and assigns each pixel a digital value corresponding to the gray level of that pixel. Accordingly, the graph of FIG. 3 illustrates the number of pixels having particular gray levels for each of three finishes of workpieces 14 as the same are viewed by the camera 20. As readily seen, each of the three curves of FIG. 3 represents a normal or "bell-shaped" distribution. For the finish denominated by the curve 40, there is a mean gray level 46 associated with the curve 40. As is well known in the field of statistics, the surface represented by the graph 40 would have a mean gray level 46, with a normal distribution of pixels as to gray level on either side of the mean 46. Similarly, the finish represented by the curve 42 is a normal distribution having a mean gray level 48, with there being a substantially equal number of pixels deviating from such mean gray level on either side. Finally, the finish denoted by the graph 44 has a mean gray level 50 associated therewith, with the normalized distribution resulting such that equal numbers of pixels of the surface image fall on either side of the mean 50 in substantially equal numbers and degrees.

In short, applicants have discovered that each of the microfinishes which have been standardized by the Bureau of Standards has a particular normalized curve associated therewith, with such curve relating the gray levels of the pixels generated from the illuminated surface. Accordingly, each standardized finish has a signature or "fingerprint" associated therewith. Further, each of the curves has been found to be of substantially identical shape, deviating primarily with respect to mean value only, when the same finishing technique is used.

Applicants have further found that when the same finish is obtained using different finishing techniques, each surface generates a bell-shaped curve having the same mean gray value and same total area under the curve, but with different curve geometry. As shown in FIG. 4, three surfaces of the same material have received the same finish, but with different techniques of finishing. For example, the surfaces having finishes depicted by the plots 52, 54, 56 are each of the same material, but the finishing technique has varied as, for example, between milled, lapped, ground, profiled, or other similar techniques. In each event, however, the gray levels of the pixels comprising the surface images share the same mean gray value 58, and in each instance the plot is normalized or "bell-shaped."

Discovering that the gray level distribution of homogeneous finished surfaces is normalized, and further discovering that the mean gray value of each normalized curve for a particular material depends upon the finish given the surface, applicants have devised a means for utilizing the system of FIG. 2 to obtain microfinish measurement. The memory 32 has stored therein data corresponding to the normalized curves of all known microfinishes of interest. By comparing the digitized image of the image memory 24 with the prestored curves, one can readily determine the finish and method of finish of a workpiece. Further, by simply knowing the material of the workpiece 14, and the type of finish being applied, the acceptability of the finish can be attained either by comparing to the known curve of the finish, or by simple comparison to the mean value of the curve. Of course, curve matching techniques are well known in the art as, for example, the least squares curve matching technique.

Figure 5:
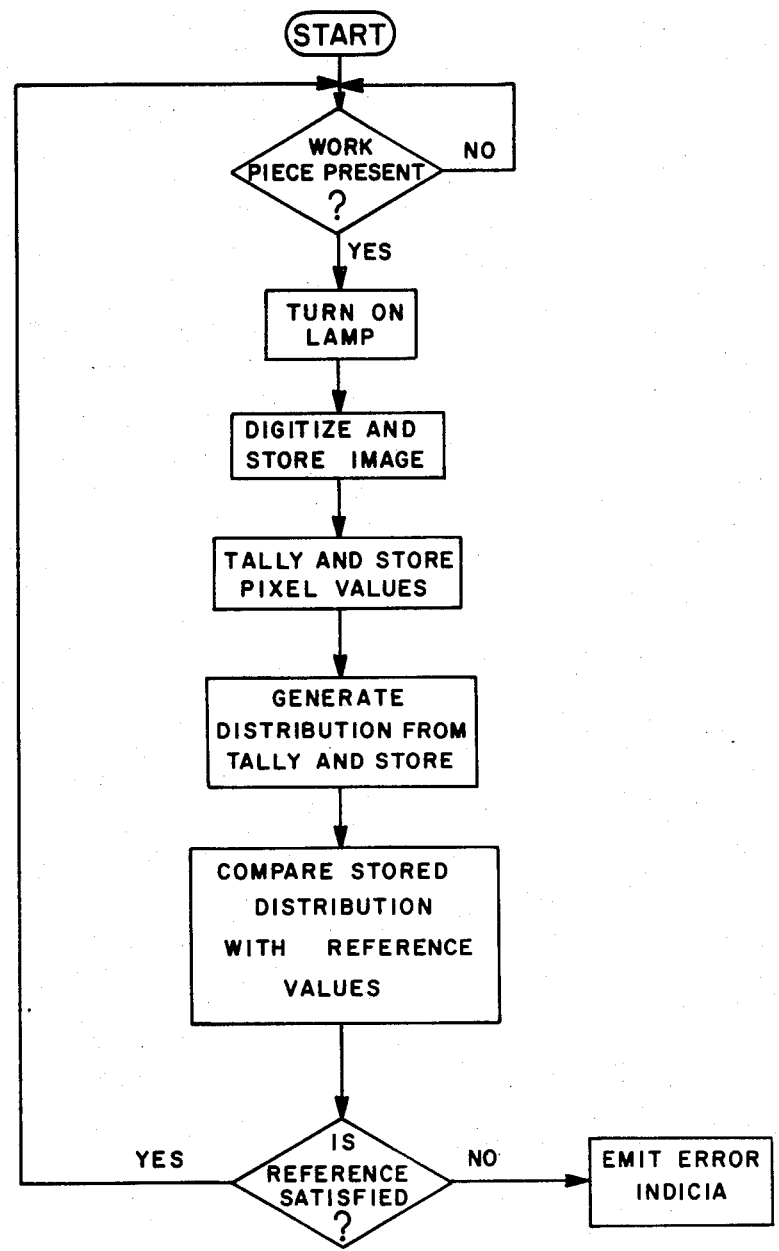
FIG. 5 is a flow chart illustrating the operation of the system of FIG. 2.

With reference now to FIG. 5, the program control flow chart for controlling the processor 30 may be seen. It will be appreciated that the program of the flow chart of FIG. 5 would typically be stored in a ROM in the memory 32. As workpieces 14 pass along the conveyor 12, the program first waits to determine whether or not a workpiece is present, such determination being made in standard fashion as by the sensor switches 38. When a workpiece is sensed as being present, the processor, through the I/O module 34, causes the lamp 18 to be illuminated. The camera 20 then generates an image of the illuminated finished surface of the workpiece 14, and the same is digitized on a pixel-by-pixel basis by the digitizer 22 and stored in the image memory 24. The processor 30 then causes a tally to be made of the pixel values of the digitized image, determining the number of pixels for each gray level which are present on the finished surface of the workpiece 14. This tally of digitized pixel gray level values is stored. Next, a distribution is generated from the stored tally of gray level values. It will be appreciated that this distribution will, for a homogeneous finished surface, constitute a normalized curve as discussed above.

With a normalized curve of the work surface stored, the program then causes the stored distribution obtained from the image memory 24 to be compared with reference values. As mentioned above, the reference values, stored in the memory 32, may comprise normalized distribution curves of known finishes and/or the mean gray level value of known finishes. If the type of finish is unknown, the program of FIG. 5 may cause a curve matching technique to be applied, seeking to match the curve generated from the digitized image with one of the pre-stored curves of known finishes. Again, curve matching techniques are well known in the mathematical and statistical fields and are not elaborated upon herein for that reason. In any event, by using a curve matching technique, the actual type of finish may be determined.

It is more likely in using the program of FIG. 5 that the material of the workpiece 14 and the finish being applied thereto would be previously known. In this instance, it would be most desired that a determination be made as to whether or not the finish meets acceptable standards. To this end, the program may simply cause the mean value of the gray level of the digitized image of the memory 24 to be compared with the known mean value of an acceptable finished surface of the same material. In such instance, the mean value may simply be tested to determine whether it falls within acceptable limits or thresholds of the mean gray level value of the stored standardized finish. Of course, even when the material and type of finish are known, it may be desired to still perform a curve matching operation to be certain that the surface has been homogeneously finished.

It will be noted from FIG. 5 that the flow chart functions to make a comparison against a reference to determine if the finish of the workpiece 14 satisfies the data of the associated reference. If not, an error signal is emitted. If the reference is satisfied, the program loops to await another workpiece.

Figure 6:
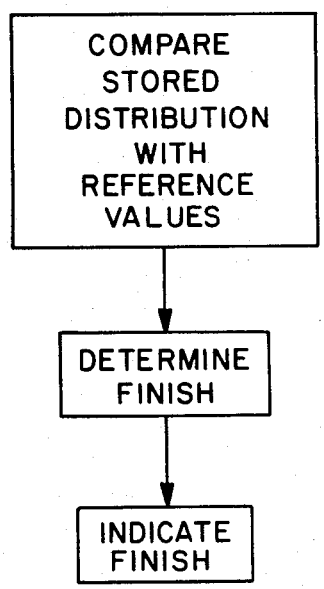
FIG. 6 is a flow chart illustration of a modification of the flow chart of FIG. 5.

FIG. 6 illustrates the change to the flow chart of FIG. 5 to allow the program to actually determine the type of finish of the workpiece. The steps of FIG. 6 would be substituted for the last three blocks of the flow chart of FIG. 5, beginning with the "compare" function. In following the modified technique of FIG. 6, the distribution of the tallied values of the digitized image of the workpiece 14 are compared by the curve matching techniques discussed above against the normalized curves of known finishes. The pre-stored curve most closely responding to the curve of the workpiece is then designated as the finish of the workpiece. With the finish so determined, it may thus be indicated as on an appropriate monitor, print-out, or the like.

It will thus be appreciated that the invention herein allows for on-line inspection of microfinishes. The operation is in real time, and is readily adapted for an assembly line application. With the lamp 18 and camera 20 fixedly mounted together, the assembly line environment will not adversely affect the operational integrity of the system. The system allows for the comparison of a known finish against a preselected acceptance criteria, while further providing means for determining the nature of an unknown finish. Utilizing the apparatus and technique of the invention, the normalized distribution curve of a surface may be compared against known curves to determine the type of finish and method of finish applied to the surface, while by comparing mean gray level values, the type of finish, irrespective of method, may be determined.

Thus it can be seen that the objects of the invention have been satisfied by the apparatus and technique presented hereinabove. While in accordance with the patent statutes only the best mode and preferred embodiment of the invention has been presented and described in detail, it is to be understood that the invention is not limited thereto or thereby. Accordingly, for an appreciation of the true scope and breadth of the invention, reference should be had to the appended claims.

What is claimed is:

1. Apparatus for determining the finish of the surface of a workpiece, comprising:
    a source of illumination;
    means for passing the workpiece into proximity with said source of illumination;
    means for generating a digitized image of the workpiece and storing digitized pixels of said image;
    storage means for maintaining data corresponding to various preselected surface finishes; and
    means for comparing said digitized pixels with said data and determining from such comparison the finish of the surface of the workpiece.

2. The apparatus as recited in claim 1 wherein said means for generating a digitized image comprises a camera and wherein said camera receives light reflected from the surface of the workpiece from said source of illumination.

3. The apparatus as recited in claim 2 which further includes means for tallying the distribution of said digitized pixels as to the gray level of each said pixel.

4. The apparatus as recited in claim 3 wherein said data is stored as a distribution of gray level values of said preselected surface finishes and wherein said means for comparing compares said distribution of said digitized pixels with said distribution of gray level values of said preselected surface finishes.

5. The apparatus as recited in claim 3 which further includes means for determining the mean value of said gray levels of said digitized pixels.

6. The apparatus according to claim 5 wherein said data is stored as to the mean gray level value of said preselected surface finishes and wherein said means for comparing compares said mean value of said gray levels of said digitized pixels with said mean gray level values of said preselected surface finishes.

7. The method of determining the acceptability of the finish of a workpiece comprising:
    illuminating said workpiece;
    generating a digitized image of a surface of said workpiece by digitizing pixels comprising said image;
    tabulating the number of pixels of each gray level within said digitized image; and comparing said tabulation with preset values obtained from surfaces of known finishes.

8. The method of claim 7 which further includes the step of determining a mean gray level value of said tabulation of pixels.

9. The method of claim 8 wherein said step of comparing comprises a comparison of said mean gray level value to a known mean value obtained from said surfaces of known finishes.

10. The method of claim 7 in which said step of comparing comprises a curve matching operation.

* * * * *